(12) United States Patent
Yoon

(10) Patent No.: US 9,204,875 B2
(45) Date of Patent: Dec. 8, 2015

(54) SUTURING INSTRUMENT CAPABLE OF SELECTING AND SUPPLYING A SUTURING THREAD

(75) Inventor: Sang Jin Yoon, Seoul (KR)

(73) Assignee: RIMSCIENCE CO., LTD., Seoul (KR)

( * ) Notice: Subject to any disclaimer, the term of this patent is extended or adjusted under 35 U.S.C. 154(b) by 955 days.

(21) Appl. No.: 13/393,056

(22) PCT Filed: Aug. 30, 2010

(86) PCT No.: PCT/KR2010/005851
§ 371 (c)(1),
(2), (4) Date: May 2, 2012

(87) PCT Pub. No.: WO2011/025337
PCT Pub. Date: Mar. 3, 2011

(65) Prior Publication Data
US 2012/0209299 A1    Aug. 16, 2012

(30) Foreign Application Priority Data
Aug. 28, 2009    (KR) .................. 10-2009-0080292

(51) Int. Cl.
*A61B 17/04*    (2006.01)
*A61B 17/12*    (2006.01)
*A61B 17/06*    (2006.01)

(52) U.S. Cl.
CPC ....... *A61B 17/0491* (2013.01); *A61B 17/06061* (2013.01); *A61B 17/06119* (2013.01)

(58) Field of Classification Search
CPC ................. A61B 17/0491; A61B 2017/0472; A61B 17/06119; A61B 17/06061; D05B 55/10; D05B 43/00

USPC ................. 606/139–150, 222–227, 232, 233; 112/470.12, 169, 221, 259, 117, 112/470.13
See application file for complete search history.

(56) References Cited

U.S. PATENT DOCUMENTS

| | | | |
|---|---|---|---|
| 4,437,465 A * | 3/1984 | Nomoto et al. ............... | 606/144 |
| 4,440,171 A * | 4/1984 | Nomoto et al. ............... | 606/145 |
| 5,651,322 A | 7/1997 | Koike | |
| 6,585,744 B1 * | 7/2003 | Griffith ......................... | 606/144 |
| 2003/0204195 A1 * | 10/2003 | Keane et al. .................. | 606/146 |
| 2004/0034372 A1 | 2/2004 | Chu | |
| 2007/0295253 A1 * | 12/2007 | Hayakawa et al. ......... | 112/102.5 |
| 2008/0035038 A1 * | 2/2008 | Ekholm et al. .................... | 112/2 |
| 2010/0242819 A1 * | 9/2010 | Fukao ............................ | 112/163 |
| 2010/0313803 A1 * | 12/2010 | Okuyama ................... | 112/102.5 |
| 2011/0011318 A1 * | 1/2011 | Fukao ............................ | 112/270 |
| 2011/0011319 A1 * | 1/2011 | Fukao ............................ | 112/302 |
| 2011/0041742 A1 * | 2/2011 | Fujihara ................... | 112/470.01 |
| 2011/0046667 A1 * | 2/2011 | Culligan et al. .............. | 606/224 |

FOREIGN PATENT DOCUMENTS

WO    9921487 A1    5/1999
WO    03090627 A2    11/2003

* cited by examiner

*Primary Examiner* — Katrina Stransky
(74) *Attorney, Agent, or Firm* — Mayer Brown LLP; Hyunho Park

(57) ABSTRACT

Provided is a suture apparatus for selecting an appropriate suture from among various sutures and supplying the selected suture. In accordance with one aspect of the present invention, there is provided a suture apparatus including: a suture keeping unit for keeping at least two types of sutures, and a suture supply unit for selectively supplying at least one of the at least two types of sutures.

17 Claims, 5 Drawing Sheets

US 9,204,875 B2

SUTURING INSTRUMENT CAPABLE OF SELECTING AND SUPPLYING A SUTURING THREAD

TECHNICAL FIELD

The present invention relates to a suture apparatus for selecting an appropriate suture from among various sutures and supplying the selected suture.

BACKGROUND ART

In a surgical operation, it is essential to suture various tissues such as a serosa, a muscle, a fascia, a skin, a blood vessel, or the like of a human body. In such a suturing process, surgical needle and various sutures may be used.

In particular, selecting an appropriate suture to suture a tissue to be sutured from among various sutures is important, and conventionally, selecting of a suture is totally dependent upon an operator's (or practitioner's) empirical knowledge. In other words, in the related art suture, the operator determines which suture is to be appropriately used in consideration of the body part of a tissue to be sutured, age, gender, and the like of a patient, totally depending on his empirical knowledge (or, occasionally, depending on his sense), and performs suturing.

DISCLOSURE

Technical Problem

However, the quality of suture fell short of some expectation due to such a practice or custom as mentioned above, and also, in fact, there was a possibility of a medical accident due to the misjudgment of the operator.

Meanwhile, the inventor of the present application, who invented a novel surgical suture apparatus, filed a related application under Korean Patent Application No. 2009-37128 which was already granted (the entire disclosure of which should be considered to be incorporated herein by reference). The inventor of this application proposes a novel technique which may be used together with the surgical suture apparatus or a similar suture apparatus to solve the related art problem as mentioned above, as follows.

Technical Solution

It is an object of the present invention to solve all of the aforementioned problems.

It is another object of the present invention to provide a suture apparatus for selecting an appropriate suture from among various sutures and supplying the same.

Advantageous Effects

In accordance with the present invention, a suture apparatus for selecting an appropriate suture from among various sutures and supplying the same can be provided.

In accordance with the present invention, the quality of suturing can be remarkably enhanced.

In accordance with the present invention, a medical accident can be prevented.

In accordance with the present invention, suturing can be more accurately and quickly performed.

DESCRIPTION OF DRAWINGS

The above objects and features of the present invention will become apparent from the following description of the preferred embodiments given in conjunction with the accompanying drawings, in which.

BEST MODE

Figure 1:
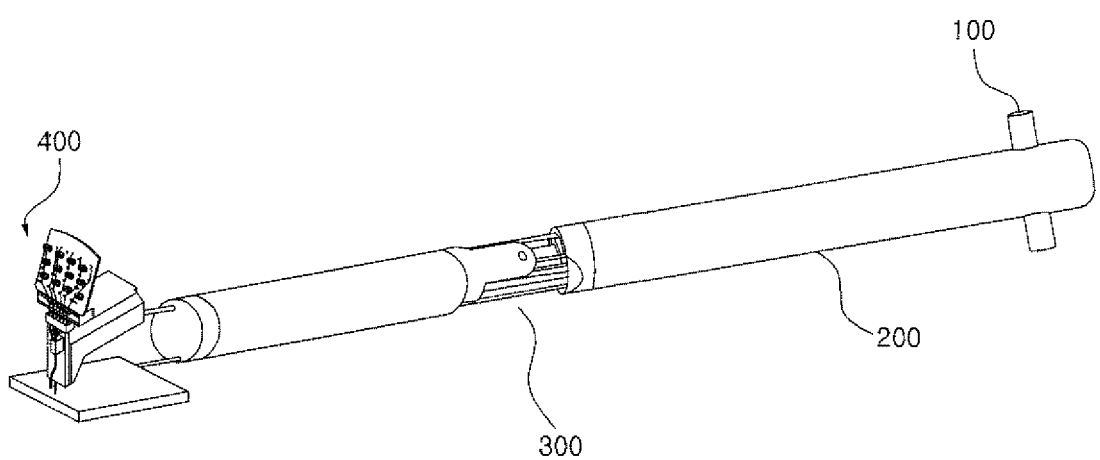
FIG. 1 is a drawing illustrating the overall configuration of a suture apparatus in accordance with an embodiment of the present invention.

Several representative configurations for achieving the aforementioned objects of the present invention are presented as follows.

In accordance with one aspect of the present invention, there is provided a suture apparatus comprising: a suture keeping unit for keeping at least two types of sutures, and a suture supply unit for selectively supplying at least one of the at least two types of sutures.

In accordance with another aspect of the present invention, there is provided a suture apparatus comprising: a support, a needle driving unit, and a surgical needle, wherein the surgical needle is accommodated in the needle driving unit to move with respect to the support, a first suture from the surgical needle and a second suture from the support are entangled according to the movement, and at least one of the first suture and the second suture is selectively supplied from a certain suture supply unit.

BEST MODE

Mode for Invention

In the following detailed description, reference is made to the accompanying drawings that show, by way of illustration, specific embodiments in which the present invention may be practiced. These embodiments are described in sufficient detail to enable those skilled in the art to practice the present invention. It is to be understood that the various embodiments of the present invention, although different, are not necessarily mutually exclusive. For example, a particular feature, structure or characteristic described herein in connection with one embodiment may be implemented within other embodiments without departing from the spirit and scope of the present invention. In addition, it is to be understood that the location or arrangement of individual elements within each disclosed embodiment may be modified without departing from the spirit and scope of the present invention. The following detailed description is, therefore, not to be taken in a limiting sense, and the scope of the present invention is defined only by the appended claims, appropriately interpreted, along with the full range of equivalents to which the claims are entitled. In the drawings, like numerals refer to the same or similar elements throughout the several views.

Hereinafter, various preferred embodiments of the present invention will be described in more detail with reference to the accompanying drawings so that a person skilled in the art can easily practice the invention.

The overall configuration and detailed components of the suture apparatus in accordance with the present invention may be similar in many parts to those of the surgical suture apparatus disclosed in Korean Patent Application No. 2009-37128 as mentioned above. Thus, hereinafter, characteristic parts and those required to be described again or additionally in the configuration of the suture apparatus in accordance with the present invention will be largely described.

Configuration of Suture Apparatus

FIG. 1 is a drawing showing the overall configuration of a suture apparatus in accordance with an embodiment of the present invention.

Referring to FIG. 1, it can be seen that a suture apparatus in accordance with an embodiment of the present invention may be configured to include a coupling part 100, a shaft part 200, an operating part 300, and a suturing part 400.

In accordance with an embodiment of the present invention, when the suture apparatus is coupled to an external device (not shown) such as a surgical robot system having a robot arm or any other surgical systems, the coupling part 100 may perform a function of receiving a certain control signal or a certain control manipulation (e.g., a mechanical control manipulation) therefrom.

In accordance with an embodiment of the present invention, the shaft part 200 is an element for connecting the coupling part 100 and the suturing part 400. Here, one or more shafts may be provided with a joint element such as the operating part 300 to allow the suture apparatus to make a joint movement. The shafts may include wires or other control attachments for controlling the suturing part 400 as explained later. Further, the shaft part 200 may serve to physically support the suture apparatus.

In accordance with an embodiment of the present invention, the operating part 300 may be disposed at the ends of or between one or more shafts of the shaft part 200 to perform a function of allowing the suture apparatus to make a joint movement and a function of determining the position and/or direction of the suturing part 400 in response to a certain control signal from an external device or a certain control manipulation. The operating part 300 may enable the suturing part 400 and/or the shafts of the shaft part 200 to move in a pitch direction and/or a yaw direction as necessary.

Hereinafter, the suturing part 400 in accordance with various embodiments of the present invention will be described in detail.

Figure 2:
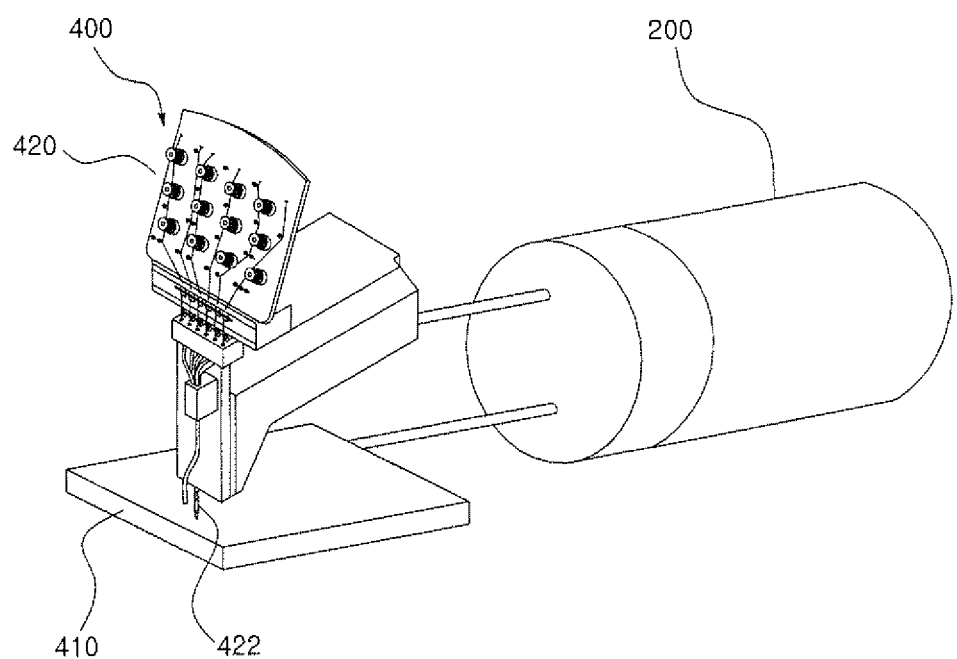
FIG. 2 is a drawing illustrating the configuration of a suturing part in accordance with an embodiment of the present invention.

FIG. 2 is a view showing the configuration of the suturing part 400 in accordance with an embodiment of the present invention.

As shown in FIG. 2, the suturing part 400 in accordance with an embodiment of the present invention may be configured to include a support 410 and a needle driving unit 420 including a surgical needle 422. Meanwhile, it is illustrated that the support 410 in accordance with the present invention is mainly a lower support 410, but it should be understood that the support 410 facing or being opposite to the surgical needle 422 may be disposed at an upper side or at a different side of the surgical needle 422.

The support 410 in accordance with an embodiment of the present invention may basically perform a function of supporting tissues to be sutured. The needle driving unit 420 in accordance with an embodiment of the present invention may perform a function of operating the surgical needle 422 with respect to the support 410. Tissues may be sutured according to the movement of the surgical needle 422. The principle of the suturing will be described with reference to FIG. 3 as follows. Also, a detailed configuration of the needle driving unit 420 in accordance with the present invention will be described with reference to FIG. 5 and the like, as follows.

In various embodiments of the present invention, various principles which are the same as or similar to those discovered in various known sewing machines for make a suture by entangling a suture from the surgical needle 422 and a suture from the support 410 may be employed.

Figure 3:
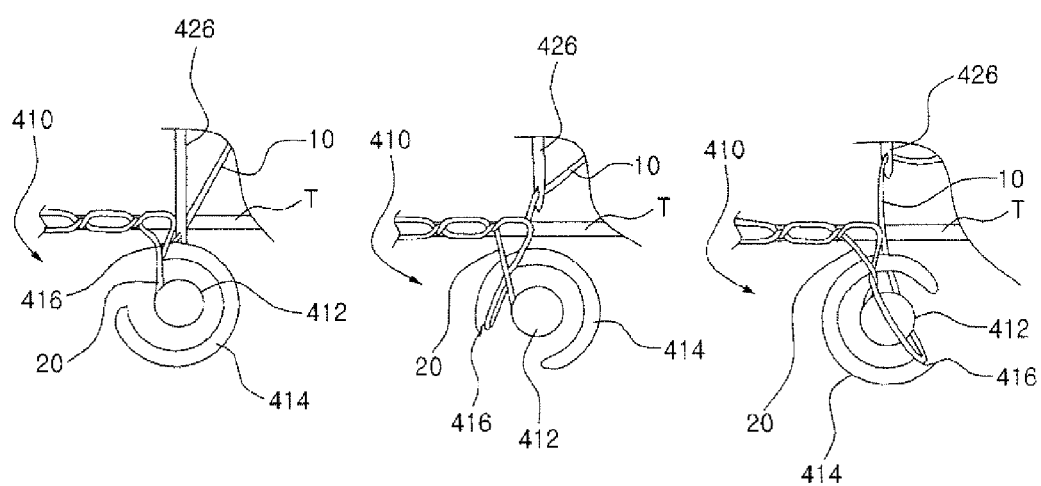
FIG. 3 is a drawing schematically showing an example of a suturing principle of a suture apparatus in accordance with the present invention.

FIG. 3 is a drawing schematically showing an example of the principle of suturing of the suture apparatus in accordance with the present invention.

As shown in FIG. 3, the surgical needle 422 may perform a reciprocal movement with respect to the support 410 (i.e., with respect to the tissue T), and in this process, the surgical needle 422 may be holding a first suture 10, preferably by a portion close to a tip thereof.

Meanwhile, the support 410, supporting the tissue T, may provide a second suture 20. To this end, the support 410 may include an internal cylinder 412 therein. Also, the support 410 may further include an external cylinder 414. The internal cylinder 412 and the external cylinder 414 may be rotated together or separately. The second suture 20 may be disposed in the internal cylinder 412 and unwound therefrom. Meanwhile, the external cylinder 414 may include a certain recess 416.

This will be described in more detail. First, as shown in the left portion of FIG. 3, when the surgical needle 422, which moves with respect to the support 410 while holding the first suture 10, penetrates the tissue T, the first suture 10 held in the surgical needle 422 is caught in the recess 416 according to the rotation of the external cylinder 414 of the support 410 to form a certain ring. Subsequently, as shown in the middle portion of FIG. 3, a second suture 20, which is unwound from the internal cylinder 412 of the support 410 according to the rotation of the internal cylinder 412, may start to enter the ring of the first suture 10 which is increased according to the continued rotation of the external cylinder 414. In this case, the surgical needle 422, still holding the first suture 10, may move in a direction away from the support 410. Finally, as shown in the right portion of FIG. 3, when the surgical needle 422 almost finishes a single reciprocal movement, a single rotation of the external cylinder 414 may be finished and the second suture 20 may enter the interior of the ring of the first suture 10, and accordingly, the first suture 10 and the second suture 20 may be entangled to suture the tissue T. In this case, the first suture 10 and the second suture 20 may be entangled but not tied. Hereafter, as the unitary suturing process described above is repeatedly performed, the overall suturing is achieved. Meanwhile, the first suture 10 and the second suture 20 may be preferably made of the same material.

In accordance with an embodiment of the present invention, the suturing part 400 may move the needle driving unit 420 according to a control signal (from an external device) or a control manipulation. For example, as an operator manipulates the external device, the needle driving unit 420 may move along with the surgical needle 422 accommodated therein with respect to the support 410. In addition, for example, as the operator manipulates the external device, the needle driving unit 420 and/or the support 410 may be driven in a direction in which suturing is performed (in this respect, if necessary, the needle driving unit 420 and/or the support 410 may be configured to move as the body length of the shaft part 200 is elongated or contracted).

Meanwhile, it should be noted that a configuration in which options for suturing (e.g., 3-layer suture, 3-line suture, 4-line suture, zigzag suture, parallel suture, hemming suture, overlook suturing, and the like) are selectable, a configuration in which suturing proceeds in an automatic mode or a semiautomatic mode, a configuration in which the space of stitches and/or the suturing speed are determined or set, a configuration in which the overall configuration or dimensions of the suture apparatus are changed as necessary so as to be appropriate for various surgical operations such as an invasive surgery, or the like may be adopted for the suture apparatus in accordance with the present invention, with reference to the description of Korean Patent Application No. 2009-37128.

Further, it should be noted that a configuration in which a rail (not shown) is applied to the needle driving unit 420, a configuration in which a rotating unit (not shown) is applied to the suturing part 400, or the like may be adopted for the suture apparatus in accordance with the present invention with further reference to the description in Korean Patent Application No. 2009-37128.

Figure 4:
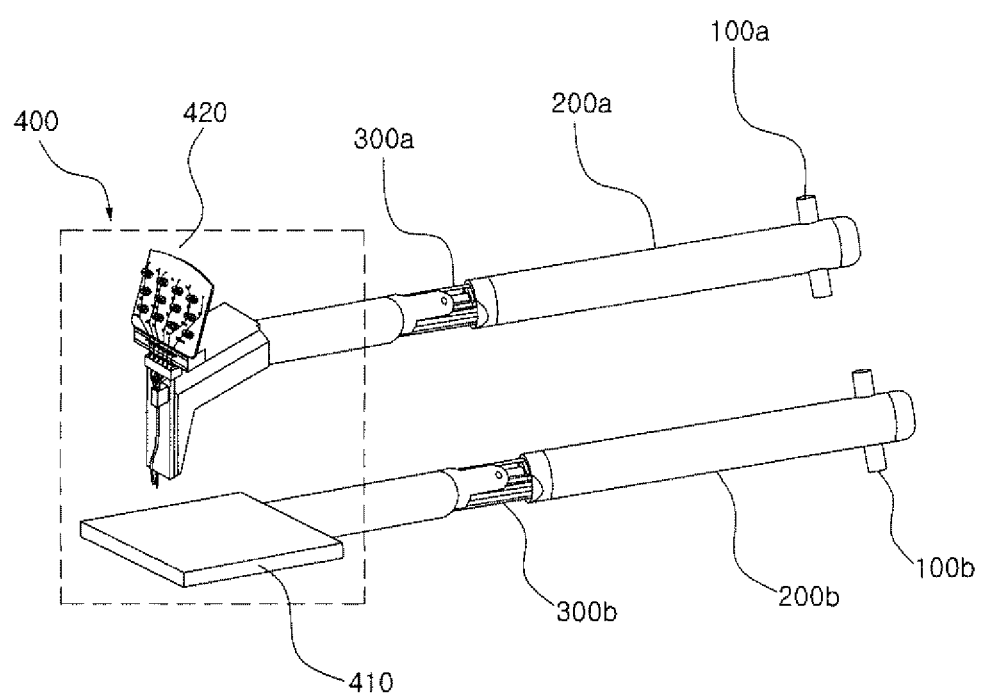
FIG. 4 is a drawing illustrating the overall configuration of a suture apparatus in accordance with another embodiment of the present invention.

FIG. 4 is a drawing showing the overall configuration of a suture apparatus in accordance with another embodiment of the present invention. As shown in FIG. 4, the suture apparatus in accordance with the present invention may have a so-called separation type configuration. That is, the suture apparatus may be configured to include a first coupling part 100*a*, a second coupling part 100*b*, a first shaft part 200*a*, a second shaft part 200*b*, a first operating part 300*a*, a second operating part 300*b*, and a suturing part 400.

In accordance with the present embodiment, as shown in FIG. 4, an upper portion of the suturing part 400 including the needle driving unit 420 as described below may form a separated module of the suture apparatus along with the first coupling part 100*a*, the first shaft part 200*a*, and the first operating part 300*a*, and as shown in FIG. 4, the support 410 corresponding to a lower portion of the suturing part 400 may form another separated module of the suture apparatus along with the second coupling part 100*b*, the second shaft part 200*b*, and the second operating part 300*b*. Here, the first coupling part 100*a*, the first shaft part 200*a*, and the first operating part 300*a* may be separated from the second coupling part 100*b*, the second shaft part 200*b*, and the second operating part 300*b*.

The respective modules of the suture apparatus having the separation type configuration in accordance with the present embodiment may approach a tissue to be sutured via various paths. Also, the joint movement in each module can be freer, and the respective modules can be controlled by different external devices. The above suture apparatus may be advantageous in case of suturing a tubular internal organ or performing suturing by using a surgical port.

Korean Patent Application No. 2009-37128 may be further referred with respect to the modified configuration of the suture apparatus in accordance with the present invention, as described above with reference to FIG. 4.

Configuration of Needle Driving Unit

Figure 5:
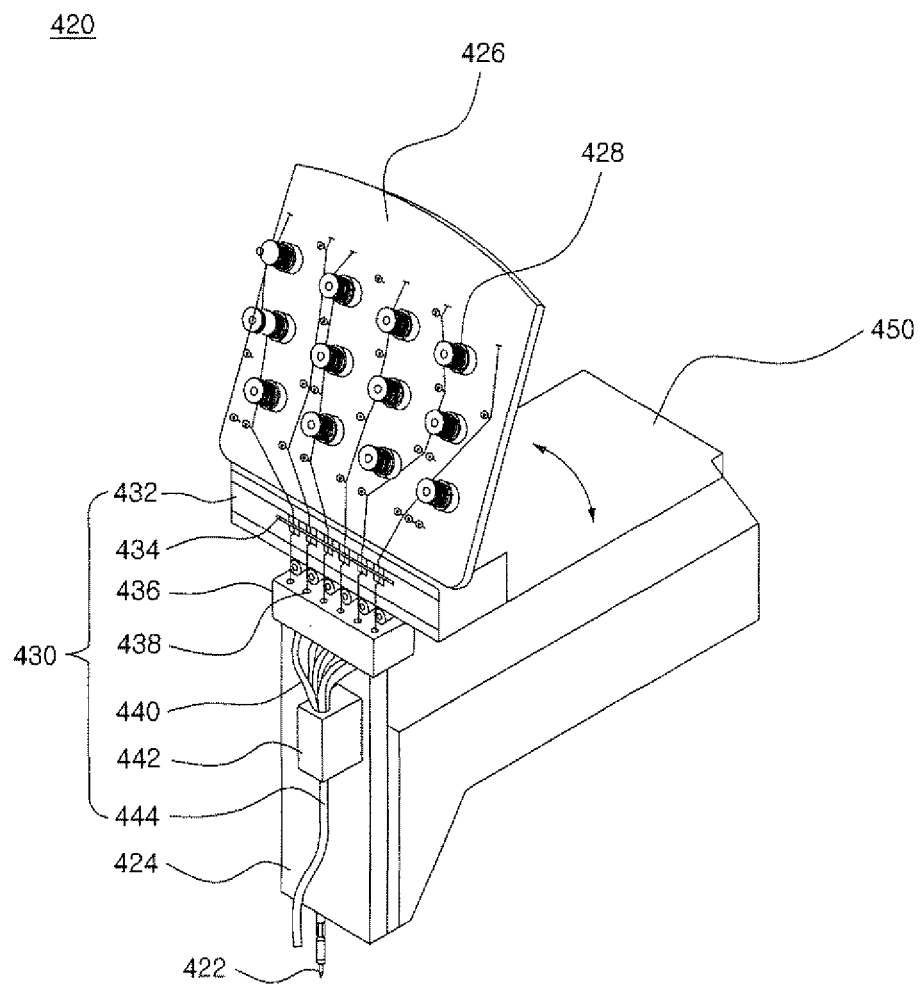
FIG. 5 is a drawing illustrating the configuration of a needle driving unit in accordance with an embodiment of the present invention.

In accordance with an embodiment of the present invention, the suture apparatus may include the needle driving unit 420 having a novel configuration for supplying an appropriate suture. FIG. 5 is a drawing showing the configuration of the needle driving unit 420 in accordance with an embodiment of the present invention.

Referring to FIG. 5, it can be seen that the needle driving unit 420 in accordance with an embodiment of the present invention may be configured to include a surgical needle 422, a needle accommodation unit 424, a suture keeping unit 426, a plurality of spools 428, a suture supply unit 430, and a shaft connection unit 450.

First, as described above, the surgical needle 422 in accordance with an embodiment of the present invention is an element configured to be able to make a reciprocal movement, while holding a suture, with respect to the support 410.

Next, the needle accommodation unit 424 in accordance with an embodiment of the present invention may move reciprocally with respect to the support 410 while accommodating the surgical needle 422, which may result in a reciprocal movement of the surgical needle 422. In order to implement the movement of the needle accommodation unit 424, a known electric or mechanical actuator (not shown) and a known driving source for driving the actuator may be variously used.

Further, the suture keeping unit 426 in accordance with an embodiment of the present invention may perform a function of keeping various sutures provided in the plurality of spools 428 disposed on the suture keeping unit 426, and providing the same to the suture supply unit 430 to be described below. Here, various sutures are preferably furnished on the suture keeping unit 426. That is, the various furnished sutures may be preferably different from each other in terms of material, tension, strength, thickness, an interior absorption time, and the like. Meanwhile, as shown in FIG. 5, the suture keeping unit 426 may be configured to be folded and unfolded in order to prevent the space occupied by the needle driving unit 420 from being excessively increased. Also, when the sutures are used up or are required to be replaced, each of the spools 428 on the suture keeping unit 426 may be easily replaced in a removable manner, or the like.

Next, the suture supply unit 430 in accordance with an embodiment of the present invention may perform a function of appropriately selecting a suture required for the surgical needle 422 and supplying the same. To this end, the suture supply unit 430 may include specific elements such as a connection attachment 432, a tension bar 434, a selection attachment 436, a plurality of holes 438, a plurality of connection pipes 440, a supply attachment 442, and a supply pipe 444.

First, the connection attachment 432 may perform a function of connecting the suture keeping unit 426 and the suture supply unit 430. Preferably, this connection by the connection attachment 432 may be easily released in preparation for a case in which the connection attachment 432 and the plurality of spools 428) are required to be replaced. To this end, various known connection means may be applied to the connection attachment 432.

Next, the tension bar 434 may serve to adjust tension of the suture according to a certain reference, when the tension of the suture provided from the suture keeping unit 426 to the suture supply unit 430 is not appropriate for supplying the suture due to a replacement of the suture keeping unit 426, a replacement of the individual spool 428, or the like.

Next, the selection attachment 436 may serve to allow only one or more sutures selected from various sutures that may be provided from the suture keeping unit 426 (two or more sutures may be supplied to the surgical needle 422 (e.g., when a suturing option such as three-line suturing is selected, or the like)) to be transferred to the connection pipe 440 (to be described below) by suction force caused by an air suction unit (not shown). To this end, the selection attachment 436 may have a plurality of holes 438 that can be selectively opened and closed. That is, each of the plurality of holes 438 may be selectively opened and closed by a certain opening and closing unit (not shown) according to a suture selection as explained below, and as a result, they can contribute to selective supply of the sutures.

Next, the supply attachment 442 may serve to transfer the suture, which has been transferred to the connection pipe 440, to the supply pipe 444. To this end, the supply attachment 442 may allow the plurality of pipes 440 to be collected as the supply pipe 444 therethrough. An air suction unit (not shown) for enabling the suture to be continuously transferred from the connection pipes 440 to the supply pipe 444 may also be provided in the supply attachment 442.

Finally, the supply pipe 444 may serve as a passage for allowing the suture which has been transferred thereto to be supplied to the surgical needle 442 therethrough. Although not shown in FIG. 5, a suture binding unit (not shown), such as a loop (not shown), for directly binding the suture in the supply pipe 444 to the surgical needle 422 may be further provided in the vicinity of the supply pipe 444. Alternatively, in order to eliminate the necessity of such a suture binding unit, a configuration in which the suture is initially bound to the surgical needle 422 on the suture keeping unit 426 may be employed. Of course, in such a case, a needle disposing unit (not shown) for disposing the surgical needle 422, which has been supplied together with the suture through the supply pipe 444 or the like, in the right position in the needle accommodation unit 424 may be required.

Further, finally, the shaft connection unit 450 in accordance with an embodiment of the present invention may serve to connect the needle driving unit 420 to the shaft part 200 as described above. The shaft connection unit 450 may be relatively freely configured according to the needs of a skilled person in the art.

Selection of Suture

As described above, a suture (preferably, the first suture 10) may be selectively supplied according to the behaviors of various elements of the needle driving unit 420. Hereinafter, the configuration of enabling the operator to select a suture will be described in detail.

In accordance with an embodiment of the present invention, the operator may select a suture provided in the spool 428 by manipulating a certain control panel (not shown) and use it. In accordance with the present embodiment, each suture selecting unit (e.g., a mechanical button or a graphical button for selecting a suture) of the control panel may be matched to an opening and closing unit of each hole 438 for selecting a suture of each spool 428. The names of body parts of tissues or other information (e.g., age, gender, and the like of a patient) may be assigned, generally as a reference in selecting a suture, to the buttons.

Meanwhile, the control panel as mentioned above or below may be freely configured by a skilled person in the art and provided in the suture apparatus in accordance with the present invention or an external device to which the suture apparatus is coupled, so long as it can control opening and closing of the plurality of holes 438 by an opening and closing unit.

In accordance with another embodiment of the present invention, an appropriate suture may be automatically selected based on a physical or chemical condition of a tissue or a periphery of the tissue that may be measured by a measurement unit (not shown) of the suture apparatus as explained hereinafter.

More specifically, the suture apparatus may further include a processor (not shown) for performing a function of automatically selecting a suture by referring to a database (not shown) which includes measurement data from the measurement unit and matches data regarding a physical or chemical condition of a tissue or the periphery of the tissue to information corresponding to an appropriate suture (e.g., identification information regarding the spool 428 or the hole 438 corresponding to the appropriate suture). This selection of a suture by the processor may be approved by the operator's manipulation on the control panel as necessary. Of course, when the operator wants to select a suture at his/her disposal, rather than the suture automatically selected by the processor, the operator's selection of a suture according to the manipulation as described above in the foregoing embodiment may be allowed.

Meanwhile, the data regarding the physical or chemical condition of a tissue or the periphery of the tissue may be pressure required for penetrating the tissue by the surgical needle 422, electric potential, pH, blood concentration or the like, the amount of moisture, and the like of the tissue or the periphery of the tissue. The measurement unit used to measure such data may be disposed on the tip of the surgical needle 422 or at a separate probe (not shown).

The foregoing measurement unit may be configured by employing one or more of various known measurement units by a skilled person in the art. For example, the pressure required for penetrating the tissue by the surgical needle 422 may be measured by a known pressurizing sensor (not shown) or pressure sensor (not shown). This sensor may measure a threshold pressure in the process of tentatively penetrating the tissue by the surgical needle 422 before performing suturing. Such a pressurizing sensor or a pressure sensor may be, for example, a component for measuring a pressurized state, a speed, or a change in speed of the needle accommodation unit 424. The threshold pressure measurement value may be transferred to the processor. Meanwhile, besides the pressurizing sensor or pressure sensor, a known measurement unit such as a known potential sensor (not shown), a pH detector (not shown) or the like may transfer the measurement data to the processor.

Further, the data measured by the measurement unit before or after the suturing may be shown to the operator through a certain display (not shown). Based on this, the operator may directly select the suture as described above or perform manipulation for updating the database as explained hereafter by using the control panel. As the operator provides such a feedback as necessary, the suturing in accordance with the present invention may be more elaborately performed.

Meanwhile, it is obvious to a skilled person in the art that the principle regarding selection and supply of a suture as described above can also be applied to the second suture 20 from the support 410 in a similar manner. For example, the second suture 20 selectively supplied from a certain second suture keeping unit (not shown) and a certain second suture supply unit (not shown) of the suture apparatus may be wound on the internal cylinder 412 of the support 410 so as to be used.

Update of Database

In accordance with a preferred embodiment of the present invention, the matching information for automatically selecting a suture stored in the database as described above may be updated according to the operator's suture selection using the control panel, as necessary. Such update may be particularly useful when the updated content of the database in an individual suture apparatus is reported to a database management server (not shown) through a certain computer communication network or a web database (not shown) on the computer communication network is commonly referred to by an individual suture apparatus. In other words, when an experienced operator selects a more appropriate suture for his/her own accord, than is automatically selected by the suture apparatus in accordance with the present invention, based on a physical or chemical condition of a tissue or a periphery of the tissue, the empirical knowledge of the operator may be used publicly through the database update.

Selective Use of Surgical Needle

The embodiment in which the suture is initially bound to the surgical needle 422 on the suture keeping unit 426 and the surgical needle 422 can be supplied together with the suture has been already described. In such a case, each suture may be bound to the surgical needle 422 which is most appropriately used together with the corresponding suture. That is, different types of surgical needles 422 may be preferably used according to characteristics such as thickness, length, strength, flexibility, and the like, as well as various different types of sutures.

In accordance with an embodiment of the present invention, based on the recognition of the foregoing matters, a configuration in which the surgical needle 422 is selectively used, apart from a suture, may be proposed. For example, a configuration in which a certain surgical needle inventory (not shown) is included in the needle accommodation unit 424, the surgical needle 422 within the inventory is selected, and a portion thereof is protruded to the outer side of the needle accommodation unit 424 so as to be used may be proposed. Such selection may be implemented according to a simple inventory rotation method. In such an implementation, it is obvious that the surgical needle 422 is selectively used by employing various components such as the measurement unit, the processor, the database, the control panel, the display, and the like, as described above. As mentioned above, the selectively supplied suture may be bound to the selected surgical needle 422 so as to be used together.

The embodiments (in particular, the embodiments regarding the process associated with the processor, the database, the control panel, the display, and the like) in accordance with the present invention as described above may be implemented in the form of program instructions that can be executed by various computer components and recorded in a computer-readable recording medium. The computer-readable recording medium may include program instructions, data files, data structures, and the like alone or in combination. The program instructions recorded in the computer-readable recording medium may be specially designed and configured for the present invention or known and available to those skilled in the field of computer software. Examples of the computer-readable recording medium include a magnetic medium such as a hard disk, a floppy disk, and a magnetic tape, an optical recording medium such as a CD-ROM and DVD, a magneto-optical medium such as a floptical disk, and a hardware device specially configured to store and execute program instructions such as a ROM, a RAM, a flash memory, and the like. Examples of the program instructions include machine language codes that are composed by a complier as well as high level language codes that can be executed by a computer using an interpreter or the like. The hardware device may be modified into one or more software modules in order to perform the process in accordance with the present invention, and vice versa.

While embodiments of the invention has been shown and described, it will be understood by those skilled in the art that various changes and modifications may be made without departing from the spirit and the scope of the invention as defined in the following claims.

What is claimed is:

1. A suture apparatus comprising:
   a surgical needle;
   a suture keeping unit for keeping at least two types of sutures; and
   a suture supply unit for selectively supplying at least one of the at least two types of sutures, wherein the selection of the suture is made with reference to data regarding a condition of a tissue to be sutured, the data being measured by a measurement unit and stored in a database.

2. The suture apparatus as claimed in claim 1, wherein the suture supply unit supplies the at least one selected suture to the surgical needle.

3. The suture apparatus as claimed in claim 1, wherein the suture supply unit supplies the at least one selected suture and the surgical needle together.

4. The suture apparatus as claimed in claim 1, further comprising:
   a plurality of spools on the suture keeping unit,
   wherein each of the plurality of spools includes at least one of the at least two types of sutures.

5. The suture apparatus as claimed in claim 1, wherein the suture supply unit includes a connection attachment for a connection with the suture keeping unit, and the connection by the connection attachment can be released.

6. The suture apparatus as claimed in claim 1, wherein the suture supply unit includes a tension bar for adjusting tension of the suture.

7. The suture apparatus as claimed in claim 1, wherein the suture supply unit includes a selection attachment for selecting the suture.

8. The suture apparatus as claimed in claim 7, wherein the selection attachment includes a plurality of holes that can be opened and closed, and each of the plurality of holes that can be opened and closed corresponds to at least one of the at least two types of sutures.

9. The suture apparatus as claimed in claim 8, wherein the suture supply unit further includes a plurality of connection pipes corresponding to the plurality of holes that can be opened and closed and a supply attachment for allowing the plurality of connection pipes to be collected.

10. The suture apparatus as claimed in claim 9, wherein the at least one selected suture is supplied from the supply attachment and is bound to the surgical needle.

11. The suture apparatus as claimed in claim 9, wherein the at least one selected suture is supplied from the supply attachment to a support for supporting the tissue.

12. The suture apparatus as claimed in claim 1, wherein the selection of the suture is made under the control of an operator.

13. The suture apparatus as claimed in claim 1, wherein the database matches the data regarding the condition of the tissue or a periphery of the tissue to information regarding an appropriate suture.

14. The suture apparatus as claimed in claim 13, wherein the data regarding the condition of the tissue or the periphery of the tissue is data regarding at least one of pressure required for penetrating the tissue with the surgical needle, electric potential of the tissue or the periphery of the tissue, pH of the tissue or the periphery of the tissue, blood concentration of the tissue or the periphery of the tissue, and the amount of moisture of the tissue or the periphery of the tissue.

15. The suture apparatus as claimed in claim 13, wherein the database can be updated according to an operator's suture selection.

16. A suture apparatus comprising:
a support for supporting a tissue to be sutured;
a needle driving unit; and
a surgical needle,
wherein the surgical needle is accommodated in the needle driving unit to move with respect to the support,
a first suture from the surgical needle and a second suture from the support are entangled according to the movement,
at least one of the first suture and the second suture is selectively supplied from a suture supply unit, and
the selection of the suture is made with reference to data regarding a condition of the tissue, the data being measured by a measurement unit and stored in a database.

17. The suture apparatus as claimed in claim 16, wherein the surgical needle is selectively supplied from a surgical needle inventory which keeps at least two types of surgical needles.

* * * * *